United States Patent [19]
Sitte et al.

[11] Patent Number: 5,226,335
[45] Date of Patent: Jul. 13, 1993

[54] AUTOMATIC INITIAL-CUTTING DEVICE FOR MICROTOMES, PARTICULARLY ULTRAMICROTOMES

[76] Inventors: Hellmuth Sitte, Reitherspitzstrasse 166, A-6100 Seefeld, Austria; Helmut Hässig, Am Gedünner 21, D-6650 Homburg-Saar, Fed. Rep. of Germany; Armin Kunz, Uhlandstrasse 19, D-6650 Homburg-Saar, Fed. Rep. of Germany; Klaus Neumann, Eichenstrasse 8, D-6652 Bexbach-Saar 5, Fed. Rep. of Germany

[21] Appl. No.: 682,954

[22] Filed: Apr. 10, 1991

[30] Foreign Application Priority Data

Apr. 11, 1990 [AT] Austria ................................. 872/90

[51] Int. Cl.⁵ .......................... G01N 1/06; B26D 5/20
[52] U.S. Cl. ............................................ 83/74; 83/72; 83/703; 83/915.005
[58] Field of Search ................. 83/13, 76, 74, 703, 83/915.5, 76.7, 72

[56] References Cited

U.S. PATENT DOCUMENTS 3,845,659  11/1974  Wikefeldt et al. ............... 83/915.5
4,691,601   9/1987  Peddinghaus .................... 83/76

FOREIGN PATENT DOCUMENTS 0052802    6/1982  European Pat. Off. ............. 83/13
3224433A1  1/1984  Fed. Rep. of Germany .
2123168A   1/1984  United Kingdom .
2130740A   6/1984  United Kingdom .

Primary Examiner—Hien H. Phan
Attorney, Agent, or Firm—Wenderoth, Lind & Ponack

[57] ABSTRACT

A device automatically applies an object (7) to a cutting edge (11) of a knife 10), and automatically makes an initial cut in the object (7), in microtomes, especially ultramicrotomes. Force sensors (27,28), length sensors (29) or other sensors, an elecrotronic control unit (25) and an encoder (22) coupled to a drive device register forces (k, −k) connected with the separation of sections by the knife edge (11) or variations in the system triggered by these forces. Subsequently, via the electronic control unit (25), a transition from a rapid speed or rate of feed to a lower cutting speed or a lesser rate of feed for making an initial cut is automatically performed. A visual and/or acoustic signal informs the user of this change. Signals ($S_1$, $S_2$) from the sensors (27-29) serve for automatic adjustment of the position of two switch-over points ($U_1$, $U_2$) from the rapid return speed ($V_R$) to the slower cutting movement ($V_S$) or from this slower cutting movement to the more rapid return movement ($V_R$). In a further development, by electronic comparison of the force/time patterns or length/time patterns, the end of the initial cutting process is established and used for a fresh automatic variation in cutting speed ($V_S$) and rate of feed.

6 Claims, 3 Drawing Sheets

AUTOMATIC INITIAL-CUTTING DEVICE FOR MICROTOMES, PARTICULARLY ULTRAMICROTOMES

BACKGROUND OF THE INVENTION

1) Field of the Invention

The invention relates to an automatic initial-cutting device for microtomes, particularly ultramicrotomes, with an object or knife moved by a driving motor. A feed movement is produced by a servomotor by way of relative movement between the knife edge and the object in order to produce sections and by at least one sensor for determining the forces resulting from separation of the sections or variations in the system which are brought about by these forces.

2) State of the Prior Art

According to the state of the art, when a microtome, particularly an ultramicrotome, is in use, considerable problems occur in connection with bringing the knife up to the object, or vice-versa. Even with enlarged viewing of the object-knife area through a microscope, which is normal on ultramicrotomes or semi-thin sectioning appliances (see in this respect H. Sitte, Ultramicrotome mta-journal extra No. 10, Umschau-Verlag Breidenstein GmbH, 1985 and; H. Sitte and K. Neumann, Ultramikrotome und apparative Hilfsmittel fuer die Ultramikrotomie, in G. Schimmel and W. Vogell, Methodensammlung der Elektronen-mikroskopie, Wissenschaftliche Verlags-GmbH Stuttgart, 1983, delivery 11), it is possible only with difficulty to achieve a binding assessment of the relative position between the object or specimen and the knife edge in the cutting area of object movement or knife movement. Problems result from the parallax error due to the fact that the optical axis of a stereo microscope is usually inclined to the path of the moving element and from the surface of the specimen, which is often irregular prior to the first cut, and from the frequently curved path of the moving part and from the general difficulty of estimating the spatial location of the moving part (e.g. the object) in relation to the fixed part (e.g. the knife edge). The result of this uncertainty is frequently either damage to the specimen and/or the knife edge upon an unintended contact between the two parts. During a first rotation ("cutting cycle") by the knife edge, a considerably too thick section may be taken from the specimen. In the event that an excessively cautious adjustment, and thus an excessively great distance between the knife edge and the object path, or vice-versa, between the area of the object on which the initial cut is to be made and the knife path, an unjustifiably large number of unsuccessful cutting cycles and thus an unjustifiably long waiting time are required from the commencement of motor movement to the taking of the first section by the knife. If the above-mentioned waiting time results, for obvious reasons, in a serious strain on the user, and in a waste of valuable working time, then as a result of the first-mentioned error, damage frequently occurs which cannot be repaired. This applies both to the damage to valuable individual objects which are often the outcome of months of preparation, or damage to valuable cutting edges, for example the valuable diamond cutting edges currently used mainly for taking ultra-thin sections.

In order to as far as possible exclude the possibility of damage or unjustifiably long waiting times, it is conventional in the state of the art to employ special feeding aids (e.g. underfloor lighting to allow adjustment by reflection) and to increase the travelling speed of the moving object or knife and/or to increase the rate of feed until the first section fragment is obtained. However, even these measures are only successful in part, because the cutting area prior to the initial cut is, in most cases, irregularly formed, and does not therefore permit of adjustment by reflection. This is because an increase in the travelling speed of the moving part makes observation of the processes even more difficult by casting shadows on the knife edge or the movement of the knife edge itself as the speed increases. Finally, there are limits to how much the rate of feed can be increased, due to the stability of the knife edge or of the specimen. In particular, with increasing the travelling speed and the rate of feed, it becomes increasingly more difficult for the user to vary both parameters at the right time after creating the first section fragment in such a way that the possibility of damage to the knife edge and/or the specimen, as a result of pieces being broken or torn away, can be reliably obviated.

SUMMARY OF THE INVENTION

Therefor, the problem which the present invention addresses is that of providing a control arrangement for microtomes, particularly ultramicrotomes of the type mentioned at the outset, by which it is possible to easily eliminate the uncertainty and risks which occur during an approach feed and initial cutting.

According to the invention, this is achieved in that at least one sensor is connected to an electronic control unit for controlling the driving motor and/or the servomotor as a function of the forces registered by the knife edge during the taking of sections form the specimens or the variations in the system brought about by these forces.

In the past, sensors, for example piezoelements or strain gauges, were used for recording forces, or the changes to the system brought about by these forces, for scientific investigations into the nature of the cutting operation, visual and acoustic displays already being utilized. In contrast, the idea underlying the invention resides essentially in using the signal from such sensors directly to control the driving motor and/or a servomotor. Thus, the travelling speed pattern (cutting speed, return speed) can be accurately and automatically established by the driving motor and the rate of feed or cutting thickness can be precisely and automatically established by the servomotor according to whether and how the specimen touches the knife edge.

Sensors of the type used show the first contact between the knife edge and the object and also the termination of this contact. Thus, start and finish of the cutting process can be precisely ascertained. In the case of an homogeneous material, since the cutting forces are dependent upon the width of cut, i.e. the dimension parallel with the knife edge, then the width or the cut or the variation in this magnitude can also be recorded by such sensors.

In the simplest case, it is possible that upon initial contact between the knife edge and the rapidly applied specimen, the sensor, via the electronic control unit, automatically reduces the travelling speed of the moving object or knife as established by the driving motor and the rate of feed or thickness of cut established by the servomotor, while at the same time triggering a visual and/or acoustic signal.

If the microtomes, particularly the ultramicrotome, is equipped with an alternating drive control arrangement, then this first signal can bring about a change-over from the rapid single drive often used when feeding and during which the object or the knife is moved steadily at a constantly high travelling speed (e.g. 100 mm/sec) to an alternating drive in which the part which is being moved is moved very slowly in the cutting zone ("cutting window", at for example 0.1 to 5 mm/sec), while in the return zone it is moved at a different and higher speed (e.g. 5 mm/sec up to 10 mm/sec).

With the use of electronic aids, developments of the invention are possible, particularly by the use of microprocessors or computers according to the state of the art. For example, a portion of slow cutting movement within the framework of the path of the part which is moving can, by means of a recording device, for example an encoder or a similar element, be used for correlating signals from a force sensor with the particular geometrical position in which the moving specimen or knife is at the instant of the signal. This position of the moving part can be subsequently reproduced, and the cutting zone can possibly be shifted on the basis of stored or preselectable data to any desired part of the overall travel of the moving part. By virtue of the characteristics of alternating drives according to the state of the art, it is impossible to perform a switch-over from rapid return movement (movement at for example 15 mm/sec) and a considerably slower cutting stroke (movement at for example 1 mm/sec), for example when the moving specimen touches the stationary knife edge and the sensor emits the appropriate signal. Since between the driving motor and a mechanism of the instrument there is at least one flexible element, for example a flexible transmission belt, which damps the motor vibrations, switch-over from the rapid return movement to the slower cutting movement gives rise to vibrations which, in the case referred to, are transmitted to the section and become visible as undulations in the section. Therefore, the switch-over must take place at, as learned by experience, a distance prior to initial contact between the knife edge and the specimen. This distance, in either time or dimension, ensures that the vibrations created during switch-over will have abated by the time of the first contact between the object and the knife. Therefore, the development of the invention resides in that, by the encoder or a similar recording device, the particular position of the object at this first signal is ascertained, and in that for the next cycle, the electronic control unit calculates the position in the path of the moving part and establishes where the change-over from return movement to cutting movement must take place if the vibrations which occur at the moment of switch-over are to have an opportunity to abate before the cutting process starts. This pattern can be repeated at every successive cycle so that, in this way, it is possible to allow for a constant change in the situation due to the geometry of the specimen and the continual removal of material from the specimen.

A further development of the invention may reside in that the change-over from the slow cutting movement to the rapid return movement is likewise established by the sensor and serves to actuate the alternating drive in so far as, directly after the section has been taken or upon disappearance of the force needed to remove the section, the alternating drive is again switched over from the slow cutting movement to the faster return movement. Since the vibrations likewise occurring because of flexible intermediate members between the driving motor and the mechanism of the microtome, particularly the ultramicrotome, cannot have any influence on the quality of the section, this change-over from slow cutting movement to rapid return movement can take place in synchronism with the second signal from the sensor without the interposition of a microprocessor or computer for shifting the position of switch-over in relation to the position at which the second signal is recorded. Therefore, the development is advantageous not only with regard to the small amount of necessary outlay involved, but in that the development at the same time minimizes the "cycle time" (the time lapse between two successive cutting processes), a minimum cycle time generally being desirable by virtue of thermal disturbances in the immediate area of the ultramicrotomy.

A further development of the invention may be that, in the case of successive cutting processes, a comparison of the pattern of signal strengths in relation to time or geometrical co-ordinates can make it possible to establish whether the size of the cutting area, when making the initial cut into the object, increases from one section to the next, or if the cutting has reached a point where now minor variations are occurring from one section to another which are caused exclusively by the geometry of the specimen (block). As a rule, even with a perfect object-knife adjustment in terms of what is possible in the method, it is not possible for the entire rough cut specimen area to already be removed in a first cut of the thickness (e.g. 5 $\mu$m or 0.1 $\mu$m), which is normal with microtomes or ultramicrotomes. Instead, there will generally be a number of fragments which represent only a part of the rough cut area (see H. Sitte, 1985, l.c., FIG. 24a, fragments $F_1$ to $F_4$) As long as such fragments are being taken, then from one cutting process to the next, the force/time pattern or the force/location pattern will change until such time as the cutting area within the scope of the new cutting series has reached the full extent of the rough cut area (see sections $U_1$ to $U_4$ of the above-quoted FIG. 24a). In the simplest case, the invention may reside in that the force/time or force/location pattern is compared over successive cutting processes, a substantial constancy being indicated to the user by a visual and/or acoustic signal, and the electronics distinguishing between the rapidly changes during initial cutting and the negligible changes during the further progress of the cutting series caused by block geometry, for example the pyramidal form of the specimen block, which is usual in ultramicrotomy, and which in this connection only takes into account the rapid variations mentioned at the outset. With an eye to working as rapid as possible, and in consideration of the limited effective life of the knife edges, particulary the glass knife edges which are frequently used in ultramicrotomy, because it is desirable to cut sections as thickly as possible until the full section area is reached, this signal allows the user to switch over the alternating drive and/or rate of feed adjustment to lesser values at what is exactly the right point in time. The system according to the invention as described, or the described pattern of section preparation on such a system, is successful not only in fresh cutting into previously cut areas, but particularly during the initial cutting of a block which has not as yet been cut. In this case, application of the knife to the object is considerably more difficult due to the absence of any reflection (see H. Sitte, l.c., pp. 22 to 22 and FIGS. 22 and 23), so that the automatic switch-over after the first contact between knife edge and block is especially advantageous. Likewise, attainment of the full area of cut during cutting of a block which has not previously been cut is often more difficult to recognize than when cutting rough cut surfaces. Since the performance during initial cutting of surfaces which have not been previously cut is similar to when cutting into previously cut blocks, this problem can also easily be overcome by the arrangement according to the invention.

An advantageous further development of the system described in the previous paragraph may reside in that the aforementioned switch-over of the alternating drive and/or the rate of feed setting to lesser values can be accomplished automatically by the system itself after a predetermined or preselectable program, and in that in a further development the change-over from one program portion to the next is indicated to the user by visual and/or acoustic signals (e.g. a brief buzzing sound).

A further development may reside in that the values automatically adjusted within the program for the cutting movement (e.g. path length and speed) and for the rate of feed (e.g. cutting thickness, number of sections and total depth of cut) can be shown, for instance on a user information display.

A further development of the invention may reside in that pairs of values, predetermined or preselectable within the program, in respect of the travelling speed of the moving part and the rate of feed of the knife and specimen towards each other (thickness of cut), can be subsequently corrected by the user according to whatever results are achieved. The adjustments are made by corresponding setting elements, for example a rotary knob, or a push button for increasing and a push button for reducing a value, the corrected values being again shown on the display.

All in all, the system according to the invention, and in accordance with the described complete development, permits a substantially automatic operation of a microtome, particularly an ultramicrotome, when making the initial cut. The long required, particularly accurate adjustment of the object and knife, which presupposes considerable experience and care on the part of the user, is largely compensated for and taken over by the automatic operation. The initial cutting process starts when there is a comparatively large distance between the knife edge and the specimen block (e.g. about 1 to 10 $\mu$m in the field of ultramicrotomy or about 0.01 to 0.1 mm in the are of ordinary microtomy), a very rapid movement of the moving part in single drive (e.g. 100 mm/sec) and a relatively high rate of feed per cycle (e.g. 2 $\mu$m in the field of ultramicrotomy) for a minimum cycle time (e.g. 1 sec). This rapid approximation does not produce any increased risk, because upon first contact between the knife edge and the specimen, the sensor emits a signal which automatically brings about the change-over to an alternating drive with a lower cutting speed and an average rate of feed/cycle, and because upon first contact between the knife edge and the object, generally only a minor fragment of the already existing or subsequently produced cutting area is removed. This setting of the cutting speed and of the rate of feed, which is modified after initial contact between the knife edge and the object, is maintained until such time as comparison of the "force/time" and/or "force/location" curves for successive cutting processes are compared and show virtually identical patterns and bring about the change-over to the definitive values for the cutting speed and the rate of feed within the framework of automatic operation. The change-over is displayed to the user. Until this point in time, in the case of the full development of the invention, the user is free from providing any manipulation. The pattern is accomplished in the shortest possible time and without the risk of any improper operation. After the final switch-over, the user has an opportunity, when required, to alter the cutting thickness or the cutting speed by however much is desirable in order to achieve the optimum results.

Finally, a clever development of this system may reside in that the forces recorded by the sensors or the signals emitted by the sensors may be picked up via an external socket on a control unit or at some other part of the system for the purpose of maintaining a continual external record, for example by means of a connected oscilloscope or recorder. This development makes it possible, in a simple way, to carry out scientific work to study the cutting process. Furthermore, within the framework of a similar development, it is possible to record the vibrations in terms of their frequency and amplitude. The force/time pattern is analyzed by an external computer, or a computer which is integrated into the electronic part of the apparatus, so that periodic changes can be detected,. Since low and high frequency vibrations are a constant problem when making ultra-thin sections (see inter aliza H. Sitte, Ultra-mikrotomie - Haufige Probleme und Fehler, in "Supplement Mikroskopie/Elektronenmikroskopie", January 1982, GIT-Verlag Ernst Giebeler, Darmstady, pages 9 to 23, particularly section 3, Vibrations, pages 11 et seq. and FIGS. 1 and 2), a display of such vibrations, particularly indicating the frequencies of amplitudes on a display constitutes a valuable aid in the preparation of ultra-thin sections. Similarly, the invention can be conveniently supplemented in that the forces recorded in the cutting process just concluded are shown on a display, the electronic unit either indicating a mean value, or by way of discrimination showing the minimum and/or maximum cutting forces.

Finally, an acoustic system, particularly a buzzer, can warn the user of forces (k, −k) when they exceed a limit value and thus prevent the preparation of sections by unsuitable means, for example an already worn out, and therefore blunt, blade.

BRIEF DESCRIPTION OF THE DRAWINGS

Further advantages and features of the invention and the developments thereof will emerge from the ensuing description of the preferred embodiments of the system according to the invention, which by way of example are show in the accompanying drawings, in which.

DETAILED DESCRIPTION OF THE EMBODIMENTS

Figure 1:
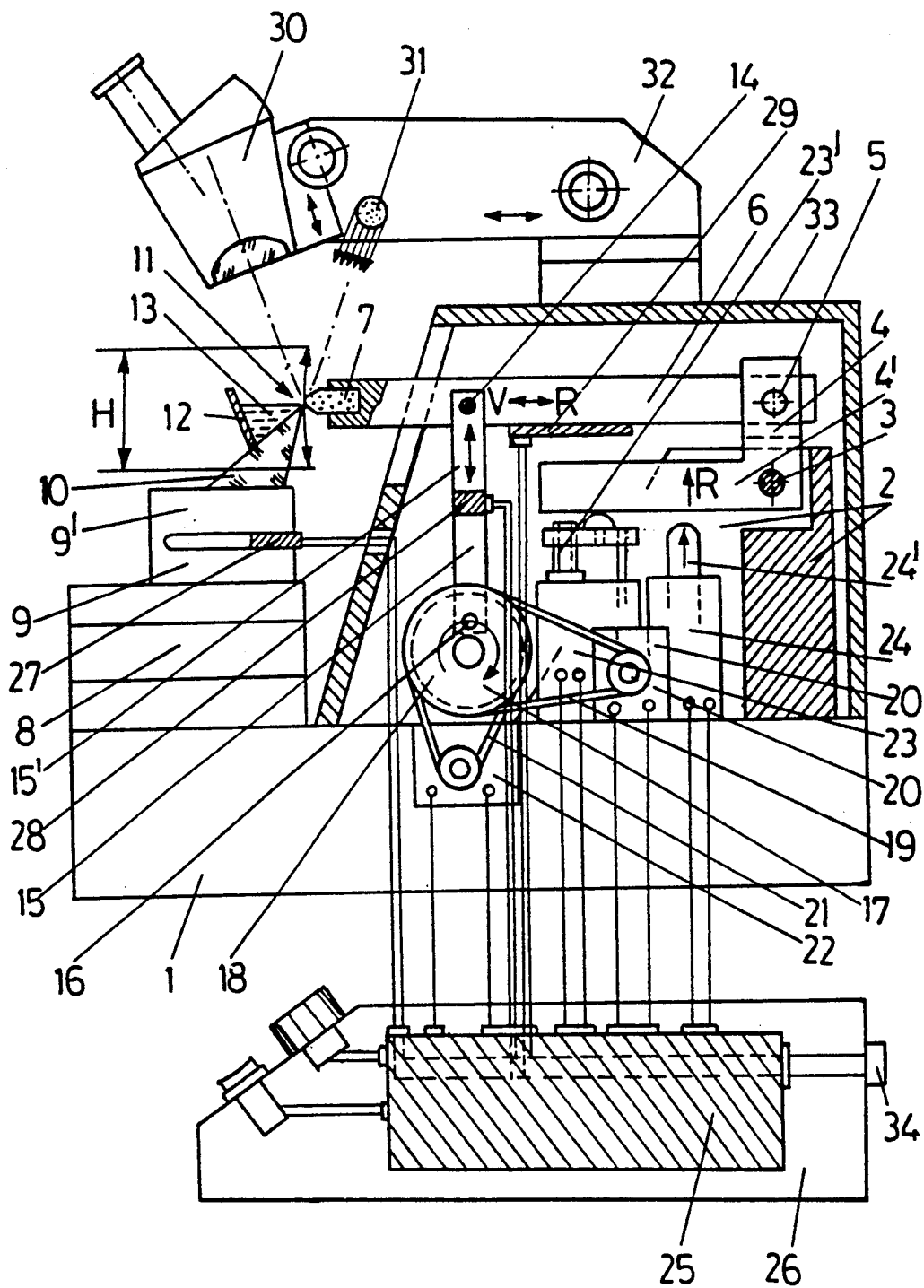
FIG. 1 is a partially sectional diagrammatic side view of an ultramicrotome showing an arrangement of force sensors, a length sensor on a knife holder and a system for supporting and guiding an object.

The apparatus shown by way of example in FIG. 1 is an ultramicrotome, the construction of which corresponds essentially to the state of the art. Mounted on a base 1 is a bearing support 2 on which, via a bearing 3, an intermediate lever 4/4' is articulated. On the lever 4/4' is articulated, via a bearing 5, a specimen carrier rod 6 with a specimen 7. Mounted on the other side of the stand or tripod 1 is a cruciform support 8 which, by means of a carrier 9/9', holds a knife 10 with a cutting edge 11. In the case of ultramicrotomes, the knife 10 is usually provided with a collecting boat 12 accommodating water 13, on the surface of which fragile ultrathin sections float. For moving a specimen, a section, a control lever 15/15' is, for example, articulated on the specimen carrier rod 6 via a bearing 14. Its bottom end is moved by a bearing 16 along a circular path which results from rotation of a disc 17 on a driven shaft 19. The disc 17 and drive shaft 18 are driven via a flexible transmission 19 and a motor 20. The rotary movement is recorded by an encoder 22, which is likewise connected via a flexible transmission 21. Both the encoder 22 and the motor 20 are connected to an electronic control unit 25 in a control drive 26. Upon rotation of the drive shaft 18 with the disc 17, an oscillating upwards and downwards movement of the rod 6 with the specimen 7 takes place. In other words, a reciprocating travel H of the specimen is created. In the field of ultramicrotomy, it has been found necessary for the specimen 7 to be passed back beside the knife edge 11 into its starting position above the knife edge ("single pass movement", see H. Sitte, 1985, 1.c.). The necessary backward return movement R is, according to the art, brought about, for instance, by a magnet 24 actuated by the electronic contact unit 25. A bolt 24' of the magnet 24, as according to FIG. 1, engages the horizontal arm 4' of the intermediate lever 4/4' during the upwards movement of the specimen 7. Furthermore, a forward feed movement V is likewise accomplished by the electronic control unit 25, which produces, for instance by means of a micrometer spindle 23' connected to a stepping motor 23, the forward feed V of the object 7 towards the knife edge 11, which movement is necessary to produce the sections. Since the cutting areas in ultramicrotomy scarcely exceed 1 sq. mm, a stereo microscope 30, having illumination 31 adjustably mounted on a support 32, which is in turn mounted on the covering 33, serves for observation of the cutting process.

Figure 2:
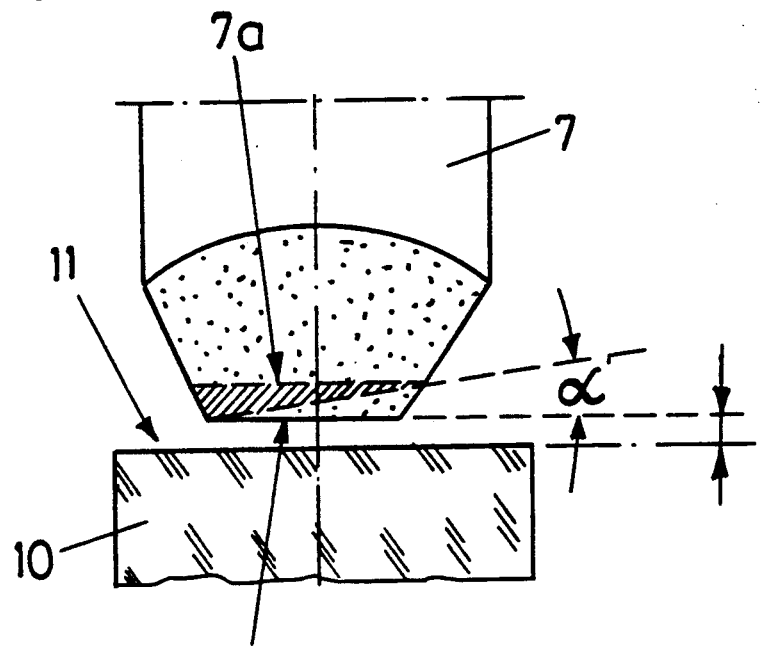
FIG. 2 is a diagrammatic front view of a rough cut surface, a side view and an elevation explaining the creation of fragments when cutting into a previously cut or rough cut surface.
Figure 2:
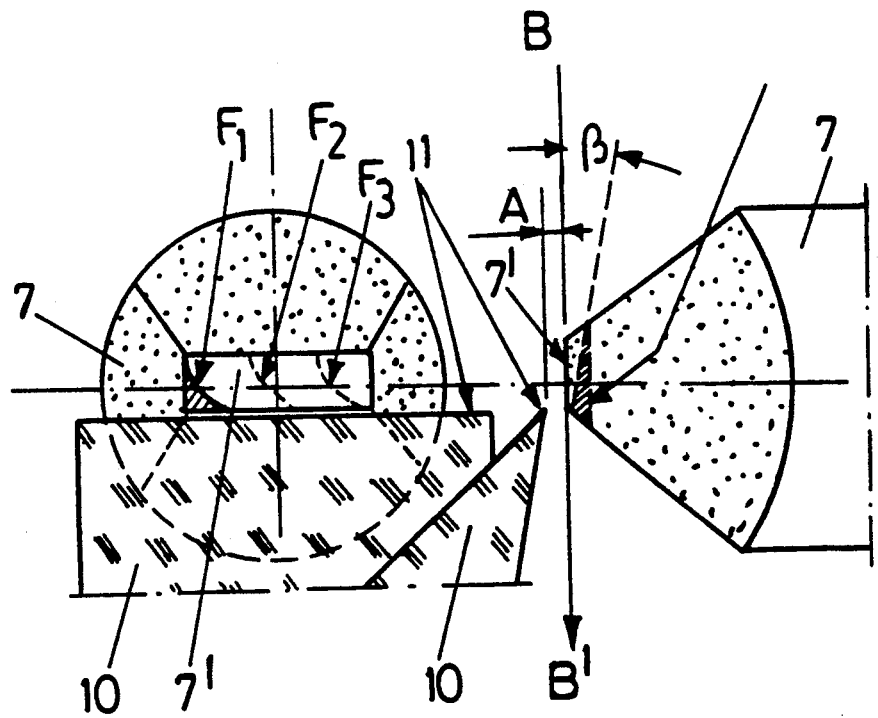

Before cutting begins, it is, noting FIG. 2, necessary for the knife edge 11 of the knife 10 to be moved ("fed") sufficiently far towards a mostly pre-cut ("trimmed") cutting area 7' of the specimen 7 so that there is only a negligible distance A left between the knife edge 11 and the cutting area 7' (see H. Sitte, 1985, 1.c.). What is important in this respect is that the cutting edge 11 of the knife 10 should be orientated exactly parallel with the cutting surface 7' of the block 7 (see front view in FIG. 2). If the area 7' is, in relation to the cutting edge 11 rotated through an angle, then it is necessary to remove material from the block until such time as a new cutting surface-7b results. Similarly, the cutting area 7' must be aligned parallel with the path BB' followed by the object 7 about the bearing 5 during the cutting movement. If the surface 7' is inclined in relation to the path BB' by an angle B (see the side view in FIG. 2), then it is necessary to initially remove material form the block 7 unit a new cutting surface 7' has been created. In both cases, the incorrect adjustment results in a considerable loss of material and time. If the cutting area has been pre-cut smoothly, then the reflection of the cutting edge 11 in the cutting area 7', with the stereo microscope 30 inclined to the path of the specimen as shown in FIG. 1, can be used for adjustment and application. Nevertheless, as already stated, this adjustment or feeding process requires considerable practice and care and represents a portion of section preparation which experience has shown to be one which creates difficulties. If the distance A is left too great, then in spite of a perfect adjustment according to FIG. 2 ($\alpha=0; B=0$), a long waiting time or a considerable number of cutting cycles will be required before the first section is produced, because for the knife and specimen there are limits imposed upon the rate of feed. If during the first pass, however, due to an incorrect adjustment or the fact that the rate of feed per cycle has been chosen to be too great, then too thick a section is taken and often the specimen becomes useless due to splitting and due to fractures or pieces being torn away, or alternatively the knife edge may be damaged. All in all, the result will be the problems discussed at the outset.

Therefore, the object of the invention is, as has likewise already been discussed, to render superfluous, at least to a great extent, the practice and expenditure of time which are vital for making the initial cut according to the state of the art by virtue of the use of automation. In the manner already described, a sensor is used which, in a per se known manner, records the forces K needed to cut off the sections or the coercive forces $-K$ which act on the cutting edge. The sensors are integrated, for example, in the form of a piezoelement 27 (FIG. 1 and FIG. 3) under the knife 10 and extending into the knife carrier 9/9', or in the form of a piezoelement 28 which is integrated into the control lever 15/15' or a strain gauge 29 which is mounted on the specimen carrier rod 6. These sensors are connected to the electronic control unit 25, which processes their signals. Generally, any sensor may be considered which with sufficient accuracy records, for example, forces, pressures or variations in length which occur during cutting, and as a result of the cutting forces. Sensors of the aforementioned type can be mounted on or integrated into all elements in the microtome engineering field, particularly those of the ultramicrotome, such instruments being exposed to forces or pressures which vary due to the cutting forces or which accomplish a change in their geometrical form, such as is the case for example with the specimen carrier rod 6, as a result of a minimal deflection.

Figure 3:
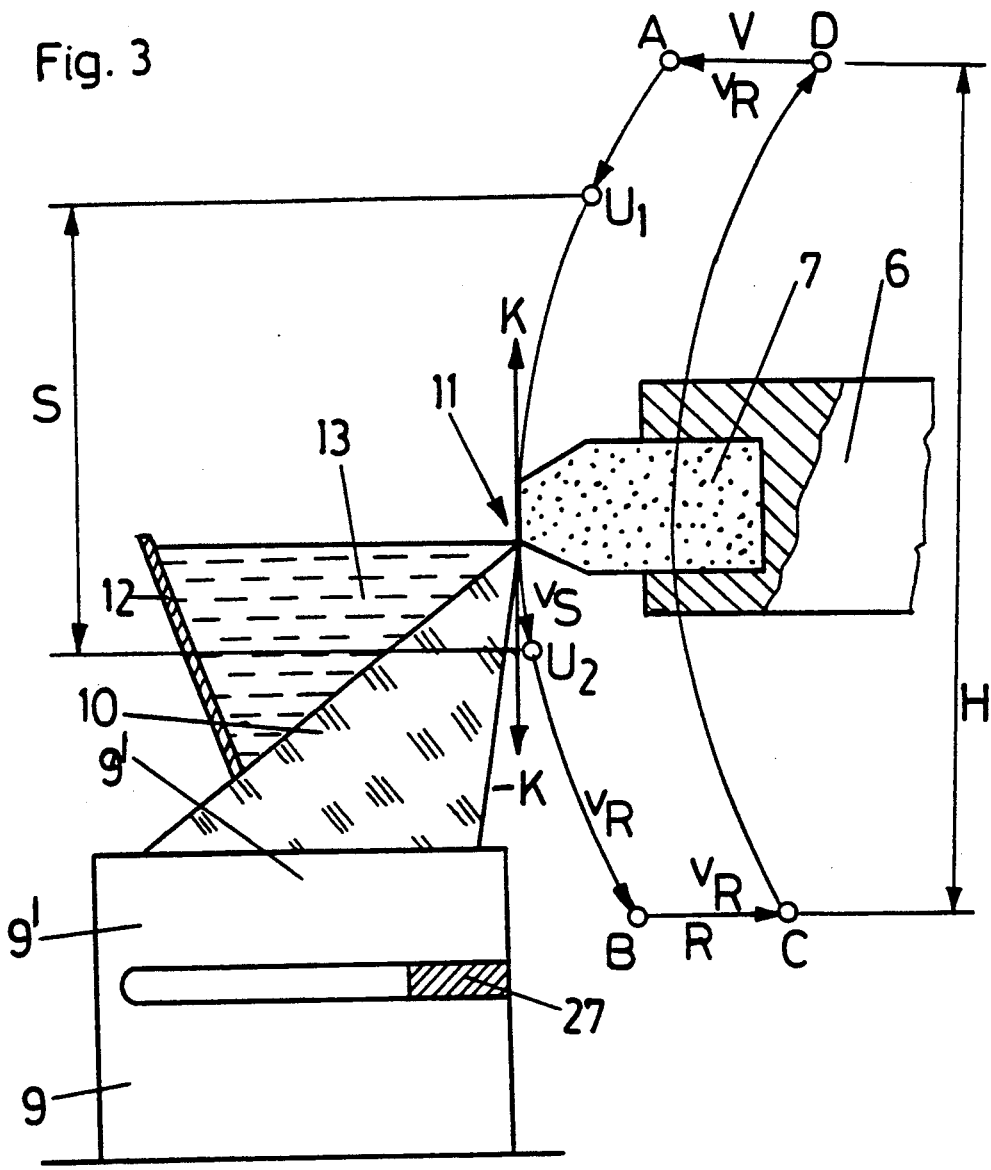
FIG. 3 is a greatly enlarged detail of an area around the object and knife of FIG. 1 explaining the pattern of movement within the framework of an alternating drive control.

Whereas feeding occurs, within limits, as quickly as possible in the manner already described, i.e. at a high travelling speed of the moving part and at a high rate of forward feed, further stages of the initial cutting take place slowly. According to the state of the art, the specimen according to FIG. 3 is in the cutting range ("cutting window" S) of the stroke H, guided slowly on its downwardly directed path with an eye to the desired minimizing of the cycle time. In the rest of the path the movement is rapid, the path extending downwardly from point A to point B. After a withdrawal R of the specimens (B → C) and movement upwards from point C to point D, the specimen, after a renewed advance V (D → A) is again in its starting position A above the knife edge 11 of the knife 10. Within the framework of alternating drive control, the travelling speed of the specimen 7 in the selected example according to FIGS. 1 and 3 is, upon reaching the first switch over point $U_1$, decelerated from the rapid return speed $v_R$ to the lower cutting speed $v_S$, and when the switch over point $U_2$ is reached, it is accelerated again up to the higher return speed $v_R$. Since this speed change can be accomplished very rapidly by electronically regulated drives, and since these rapid changes are vital in terms of reproducible movement patterns and the desired minimum cycle time, then both during deceleration ($U_1$) and also upon renewed acceleration ($U_2$), and as a result of the flexible transmission 19 (FIG. 1), vibrations occur. These vibrations must have abated prior to taking of the section, since otherwise they will be manifest in the form of periodically thicker and thinner zones in the section ("chatter" or "undulations"), rendering the section unusable. Usually, as indicated in FIG. 3, the cutting window S is asymmetrically disposed so that the first switch over $U_1$ takes place at a greater distance above the cutting edge 11 of the knife 10 and so that in contrast, the second switch over $U_2$ takes place, as far as is possible, immediately upon conclusion of section removal, so that the cycle time is kept as short as possible. Apart from feeding to as far as possible a minimal but reliably reproducible distance A, the correct disposition of the cutting window S will in practice and on the grounds already outlined produce the serious difficulties which can be eliminated by the automatic initial cutting system according to the invention.

Figure 4:
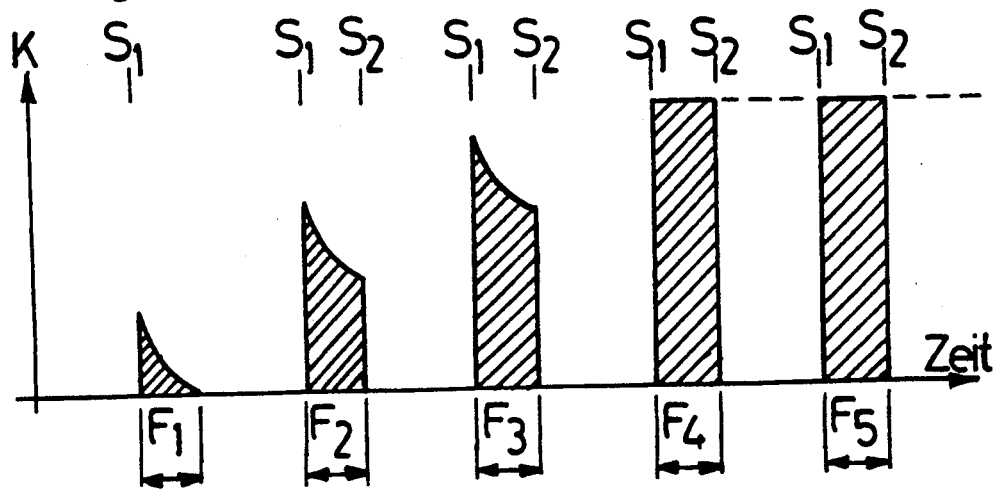
FIG. 4 shows an example of a force/time pattern when cutting into an object of the type shown diagrammatically in FIG. 2.

It is possible, according to the invention, for the first contact between the object and the cutting edge 11 of the knife 10 to be defined on a basis of the first signal from a sensor 27, 28 or 29, both in terms of time and also, by means of the encoder 22, in terms of location, after which the position of the switch-over point $U_1$ or its distance from the knife edge can be so established on the basis of empirical values for the subsequent cutting cycles that the vibrations already defined in the proceeding description, and which occur at switch-over, can have abated by the time the next process commences. As a rule, upon first contact between the knife edge 11 and the object 7, only a fragment $F_1$ is taken from the object 7, and its form is shown by way of example in the front view in FIG. 2. The force/time pattern which can be anticipated according to this example, and which is recorded by the sensor 27 or 29, is shown diagrammatically in the area $F_1$ in FIG. 4. It can be seen that in this case, at least one signal ($S_1$) is sufficiently clear for the switch-over from the fast drive to the slower alternating drive to be accomplished automatically in the manner already described. In the subsequent cutting cycles, the fragments $F_2$, $F_3$ and $F_4$ are taken, the dimensions of the fragments increasing steadily from $F_2$ to $F_4$. In the following fifth cutting cycle, within the framework of this example, which corresponds to cutting practice, the cutting process is concluded. No later than upon conclusion of this cutting process, the force/time pattern will achieve the form shown diagrammatically for the fragment $F_4$ in FIG. 4 in which both signals $S_1$ and $S_2$ are acquired and processed by the electronic unit with a high $dR/d_t$. Thus, for cutting areas according to FIG. 2 having two edges parallel with the knife cutting edge 11, a further feature of the invention is possible in which the first signal $S_1$ according to FIG. 4 is used for automatic fixing of the switch-over point $U_1$ while the second signal $S_2$ is used to trigger the switch-over $U_2$. Automatic fixing of the -over point $U_1$ takes place on a basis of empirical values which establish the duration of vibrations triggered by the switch-over $U_1$ and take into account the predetermined or preselected travelling speeds $v_R$ and $v_S$. In this respect, the geometrical location at which the specimen 7 contacts the cutting edge 11 of the knife 10 is known from the signal $S_1$ via the encoder 22. Therefore, it is possible to calculate through the electronic facility and from the indicated signal $S_1$ and the indicated values of the locations where the change over $U_1$ is to take place when the aforementioned condition is to be satisfied. Once again, the driving motor 20 is actuated by the electronic control unit 25 by means of the encoder 22. The switch over $U_2$ is triggered by this control unit 25 directly by the signal $S_2$, as already described above.

A further feature of the invention resides in the manner already described above wherein the force/time patterns in the portions $F_1$, $F_2$ and $F_3$ have to be compared and a conclusion drawn therefrom as to the cycle in which the cutting process is concluded. Within the framework of the example given with reference to FIGS. 2 and 4, the force/time pattern varies form $F_1$ to $F_2$, from $F_2$ to $F_3$ and from $F_3$ to $F_4$, whereas in the subsequent cycles $F_5$ and so on it remains virtually constant if one disregards the constant increase in forces or extension of the time portions predetermined by the pyramidal shape of the block portion, but which can, however, be easily distinguished from the variations in the area $F_1 \rightarrow F_4$ by the electronic control unit 25. By the comparison between the portions $F_4$ and $F_5$, the completion of this initial culling process can be readily established. Therefore, the electronic control unit 25 switches over automatically in the manner already described switch to a lower cutting thickness and a lower travelling speed and gives the user a visual and/or acoustic signal.

In the manner already described above, a further feature of the invention resides in the conclusion of the automatic feeding described in the previous portion, or after the signal and the final change-over by two separate adjusting elements, for example by two rotary potentiometers which automatically, and in the cutting area, correct the predetermined travelling speed $v_S$ of the object of the automatically predetermined rate of feed. They thus optimize the manual intervention needed for parameters which decide the cutting operations. The preselected pair of values, modified within the scope of correction and relating to cutting speed and rate of feed, are shown on a display or in some other manner.

Finally, a further feature of the invention is possible in that the signals from the sensor 27, 28 or 29 can, according to FIG. 1, be fed to a socket 34, which may be disposed, for example, on cladding 26 of the control unit. The signals can then be picked up externally and evaluated by a downstream system. In an alternative form of this feature, it is possible for the evaluation to be carried out in the manner already described, but within the system, by the use of corresponding elements of the electronic control unit 25. The results produced can be shown on the instrument, for example on a display of the control device 26.

By way of adaptation to the varying needs of practice and varying constructions of microtome and sea-thin cutters, and in particular ultramicrotomes of different construction and combinations, it is possible for the invention to be carried into effect without any compromise to its inventive character. In particular, the invention can be carried into effect with various holders which may be different from the ultramicrotome system shown in FIG. 1 and with movements of the object or knife which may different. This is true of slide or basic slide microtomes or rotational (minot) microtomes of conventional construction with an exclusively rectilinear and non-circular guidance of the specimen or knife. The forward feed is accomplished via servomotors, and the cutting movements takes place automatically or via a motor drive by means of an electronic control unit, which is preferably connected to a system corresponding to an encoder (angle coder).

In particular, the automatic feeding and cutting can be carried out, in the case of microtomes, within the meaning of the invention, but with no alternating drive control facility. Rather, feeding, initial cutting and cutting are accomplished, in each case, at differing travelling speeds of the moving part and with at least partially differing rates of feed. It is immaterial whether it is the object or the knife, after the section has been taken, that is temporarily removed, the one from the other, by a relative movement, within the meaning of the "single-pass principle", as is described by way of example with reference to elements 24/24'/4'/4/6 within the framework of the withdrawal R, and in FIGS. 1 and 3. It is immaterial whether a force/time pattern is recorded by means of a pressure or force sensor or whether at this point a homologous length/time pattern or other pattern is registered by some other kind of sensor, for example a strain gauge, used for control purposes.

Likewise, it is immaterial, and certainly immaterial for implementation of the invention, whether instead of the aformentioned piezoelements or strain gauges other sensors or arrangements are used for measuring forces, pressures or variations in length, so long as they guarantee the accuracy and speed of reaction needed to carry out the invention. Furthermore, for implementation of the idea underlying the invention it is immaterial how and by which elements the various travelling speeds $v_S$ or $v_R$ of whichever is the moving part and the rates of feed (cutting thicknesses) are selected, altered and indicated to the user. The same applies to the nature of the signals which inform the user about variations in individual parameters or the various functioning cycles.

We claim:

1. An automatic initial cutting device in a microtome, comprising:
   a knife having an edge for cutting an object;
   holding means for holding the object to be cut by said knife;
   a driving means operably connected to one of said knife and said holding means for relative movement therebetween at a travelling speed for cutting the object;
   feed means for producing a relative feed movement between said knife edge and said holding means such that the object can be sectioned by said knife edge, said feed means comprising a servomotor;
   sensing means, comprising at least one sensor, for sensing a condition resulting from forces generated by said knife edge cutting a section of the object and generating a signal corresponding to the condition sensed; and
   an electronic control means for receiving said signal from said sensing means and controlling at least one of said driving means and servomotor of said feed means as a function of the condition resulting from the forces generated by said knife edge cutting a section of the object, wherein said electronic control means controls said driving means to generate a first relatively rapid and constant travelling speed between said knife and said holding means, automatically switches over from the first travelling speed to a second, reduced cutting speed outside of said cutting zone, said cutting zone being defined as a function of said signal from said sensing means.

2. The automatic initial cutting device in a microtome of claim 1, wherein said electronic control means switches over to said return speed from said reduced cutting speed based on said signal from said sensing means indicating an end of cutting between said knife edge and an object held by said holding means.

3. An automatic initial cutting device in a microtome, comprising:
   a knife having an edge for cutting an object;
   holding means for holding the object to be cut by said knife;
   a driving means operably connected to one of said knife and said holding means for relative movement therebetween at a travelling speed for cutting the object;
   feed means for producing a relative feed movement between said knife edge and said holding means such that the object can be sectioned by said knife edge, said feed means comprising a servomotor;
   sensing means, comprising at least one sensor, for sensing a condition resulting from forces generated by said knife edge cutting a section of the object and generating a signal corresponding to the condition sensed;
   an electronic control means for receiving said signal from said sensing means and controlling at least one of said driving means and servomotor of said feed means as a function of the condition resulting from the forces generated by said knife edge cutting a section of the object; and
   a recording device connected to said electronic control means for recording the relative position of said knife edge and an object held by said holding means and indicating the relative position to said electronic control means, wherein said electronic means controls said driving means as a function of said signal from said sensing means when the object held by said holding means contacts said knife edge and the indication from said recording device to switch from a rapid relative speed between said knife and the object held by said holding means to a slower cutting speed at a position before contract between said knife edge and the object such that vibrations arising from switching over from the rapid relative speed to the slower cutting speed have abated before contact between said knife edge and the object takes place.

4. An automatic initial cutting device in a microtome, comprising:
   a knife having an edge for cutting an object;
   holding means for holding the object to be cut by said knife;
   a driving means operably connected to one of said knife and said holding means for relative movement therebetween at a travelling speed for cutting the object;
   feed means for producing a relative feed movement between said knife edge and said holding means such that the object can be sectioned by said knife edge, said feed means comprising a servomotor;

sensing means, comprising at least one sensor, for sensing a condition resulting from forces generated by said knife edge cutting a section of the object and generating a signal corresponding to the condition sensed; and an electronic control means for receiving said signal from said sensing means and controlling at least one of said driving means and servomotor of said feed means as a function of the condition resulting from the forces generated by said knife edge cutting a section of the object, wherein said electronic control means controls said driving means and said feed means such that said knife edge can repeatedly cut sections from an object held by said holding means, said electronic control means comparing said signals from said sensing means for successive sections cut from the object and switching at least one of said driving means and said feed means to a low cutting speed, or low rate of feed or cutting thickness, respectively, when substantially identical said signals result from two consecutive sections cut from the object.

5. The automatic initial cutting device in a microtome of claim 4, and further comprising means for manually correcting the values of the low cutting speed and low rate of feed or cutting thickness set by said electronic control means within predetermined limits.

6. An automatic initial cutting device in a microtome, comprising:

a knife having an edge for cutting an object;

holding means for holding the object to be cut by said knife;

a driving means operably connected to one of said knife and said holding means for relative movement therebetween at a travelling speed for cutting the object;

feed means for producing a relative feed movement between said knife edge and said holding means such that the object can be sectioned by said knife edge, said feed means comprising a servomotor;

sensing means, comprising at least one sensor, for sensing a condition resulting from forces generated by said knife edge cutting a section of the object and generating a signal corresponding to the condition sensed;

an electronic control means for receiving said signal from said sensing means and controlling at least one of said driving means and servomotor of said feed means as a function of the condition resulting from the forces generated by said knife edge cutting a section of the object;

a display means for displaying to a user at least one of the minimum and maximum forces resulting from said knife edge cutting a section of the object, said display means displaying the forces from the most recent cutting of a section of the object, and the forces being determined from said signal of said sensing means; and signalling means for signalling a user when one of the minimum and maximum forces falls below or exceeds a predetermined value.

* * * * *